(12) United States Patent
Rothfritz et al.

(10) Patent No.: US 6,192,734 B1
(45) Date of Patent: Feb. 27, 2001

(54) DISPOSABLE CALIBRATION TARGET

(75) Inventors: Robert Rothfritz, Marietta; Scott Kerr, Stone Mountain; Glenn Steven Arche; Scott Kellogg, both of Duluth; Gregory J. Newman, Atlanta; Mark A. Samuels, Norcross; Richard Lachlan Fowler, Lawrenceville, all of GA (US)

(73) Assignee: SpectRx, Inc, Norcross, GA (US)

( * ) Notice: Subject to any disclaimer, the term of this patent is extended or adjusted under 35 U.S.C. 154(b) by 0 days.

(21) Appl. No.: 09/286,649

(22) Filed: Apr. 6, 1999

Related U.S. Application Data (63) Continuation of application No. 09/054,490, filed on Apr. 3, 1998, now Pat. No. 5,924,981, which is a continuation-in-part of application No. 08/904,766, filed on Aug. 1, 1997, now Pat. No. 5,924,981, which is a continuation-in-part of application No. 08/621,182, filed on Mar. 21, 1996, now abandoned, which is a continuation-in-part of application No. 08/587,949, filed on Jan. 17, 1996, now Pat. No. 5,860,421.

(51) Int. Cl.[7] .................... A61B 5/00; A61B 6/00; G01D 18/00; G01N 3/62

(52) U.S. Cl. ............... 73/1.01; 600/300; 600/306; 600/315; 600/473

(58) Field of Search ............. 73/1.01, 620, 621; 178/18.09; 250/491.1; 356/243, 244; 378/18, 207; 600/315, 306, 309, 310, 473, 476, 477

(56) References Cited

U.S. PATENT DOCUMENTS

| | | |
|---|---|---|
| 3,677,652 | 7/1972 | Little ................................. 356/183 |
| 4,029,085 | 6/1977 | DeWitt et al. ...................... 128/2 |
| 4,177,798 | 12/1979 | Leveque et al. . |
| 4,241,738 | 12/1980 | Lubbers et al. . |
| 4,267,844 | 5/1981 | Yamanishi ......................... 128/633 |
| 4,322,164 | 3/1982 | Shaw et al. ........................ 356/243 |
| 4,344,438 | 8/1982 | Schultz . |
| 4,360,270 | 11/1982 | Jeck ................................... 356/243 |
| 4,423,736 | 1/1984 | DeWitt et al. . |

(List continued on next page.)

FOREIGN PATENT DOCUMENTS 747 002 A1  11/1996  (EP) .............................. A61B/5/00

* cited by examiner

*Primary Examiner*—Hezron Williams
*Assistant Examiner*—Dennis Loo
(74) *Attorney, Agent, or Firm*—Fleshner & Kim, LLP (57) ABSTRACT

A combined infection shield and calibration or reference target for use with a measuring instrument includes a removable calibration/reference layer. The removable calibration/reference layer has predetermined optical characteristics that can be utilized to calibrate or reference the instrument. When the calibration/reference layer is removed from the remaining portions of the device, the portion of the calibration/reference layer having the predetermined optical characteristics is irrevocably altered such that the calibration/reference layer cannot be reused. The combined infection shield and target may be attached to a shield holder, which in turn is attached to an instrument. Alternatively, the infection shield and target may be attached directly to an instrument. The target may include a calibration/reference layer having a reduced strength portion which causes the target to tear or separate in a predetermined manner. Also, a double-sided adhesive layer with a gap may be used to attach the target to the remaining portions of the device, wherein the gap is arranged in a predetermined orientation with the reduced strength portion to aid tearing or separation of the target in a predetermined manner. The device may also include a cutter for causing the calibration/reference layer to tear or separate in a predetermined manner when the calibration/reference layer is removed from other portions of the device.

22 Claims, 5 Drawing Sheets

U.S. PATENT DOCUMENTS

| | | | |
|---|---|---|---|
| 4,495,413 | 1/1985 | Lerche et al. | 250/252.1 |
| 4,499,375 | 2/1985 | Jaszczak | 250/252.1 |
| 4,500,782 | 2/1985 | Allemann et al. | 250/291 |
| 4,642,422 | 2/1987 | Garwin et al. | 178/18 |
| 4,700,708 | 10/1987 | New et al. | 128/633 |
| 4,744,656 | 5/1988 | Moran et al. | 356/243 |
| 4,768,516 | 9/1988 | Stoddart et al. . | |
| 4,770,179 | 9/1988 | New et al. | 128/633 |
| 4,790,324 | 12/1988 | O'Hara et al. . | |
| 4,796,633 | 1/1989 | Zwirkoski | 128/634 |
| 4,847,493 | 7/1989 | Sodal et al. | 250/252.1 |
| 4,867,557 | 9/1989 | Takatani et al. . | |
| 4,894,547 | 1/1990 | Lefell et al. . | |
| 4,911,559 | 3/1990 | Meyst et al. . | |
| 4,914,720 | 4/1990 | Knodle et al. | 250/343 |
| 4,975,581 | 12/1990 | Robinson et al. | 250/339 |
| 4,981,355 | 1/1991 | Higgins | 356/243 |
| 5,030,986 | 7/1991 | Dwyer et al. | 355/20 |
| 5,088,834 | 2/1992 | Howe et al. . | |
| 5,119,819 | 6/1992 | Thomas et al. . | |
| 5,146,091 | 9/1992 | Knudson . | |
| 5,169,235 | 12/1992 | Tominaga et al. . | |
| 5,311,273 | 5/1994 | Tank et al. | 356/43 |
| 5,337,289 | 8/1994 | Fashing et al. | 367/140 |
| 5,349,961 | 9/1994 | Stoddart et al. . | |
| 5,353,790 | 10/1994 | Jacques et al. | 128/633 |
| 5,355,880 | 10/1994 | Thomas et al. . | |
| 5,360,004 | 11/1994 | Purdy et al. . | |
| 5,365,925 | 11/1994 | Lee | 128/634 |
| 5,371,358 | 12/1994 | Chang et al. | 250/226 |
| 5,383,452 | 1/1995 | Buchert . | |
| 5,411,032 | 5/1995 | Esseff et al. . | |
| 5,416,816 | 5/1995 | Wenstrup et al. | 378/18 |
| 5,435,309 | 7/1995 | Thomas et al. . | |
| 5,458,140 | 10/1995 | Eppstein et al. . | |
| 5,487,607 | 1/1996 | Makita et al. . | |
| 5,792,049 | 8/1998 | Eppstein et al. | 600/306 |
| 5,924,981 * | 7/1999 | Rothfritz et al. | 600/306 |

DISPOSABLE CALIBRATION TARGET

This application is a continuation of U.S. patent application No. 09/054,490, filed Apr. 3, 1998 now U.S. Pat. No. 5,924,981, which is a continuation-in-part of U.S. patent application Ser. No. 08/904,766, filed Aug. 1, 1997 now U.S. Pat. No. 5,924,981, which in turn is a continuation-in-part of U.S. patent application Ser. No. 08/621,182, filed Mar. 21, 1996 now abandoned, which in turn is a continuation-in-part of U.S. patent application Ser. No. 08/587,949, filed Jan. 17, 1996 now U.S. Pat No. 5,860,421. The contents of all four parent applications are hereby incorporated by reference.

BACKGROUND OF THE INVENTION

1. Field of the Invention

The invention relates to an infection shield and a calibration or reference device for calibrating a measuring instrument or serving as a reference target. The invention also relates to methods of taking a reading or measurement of a patient or an object using the calibration or reference device.

2. Background of the Related Art

There are a variety of measuring instruments that utilize light to detect physical characteristics or conditions of a material. Some instruments are used by medical personnel to diagnose a condition of a patient.

In the case of medical instruments, the instrument will emit light at one or more wavelengths, and the emitted light is directed toward a target tissue on a patient. Reflected or scattered light that returns from the target tissue, or possibly fluorescent light generated by the target tissue in response to the emitted light, is then collected by the medical instrument and analyzed to determine characteristics of the target tissue, or a condition of the patient.

Figure 1:
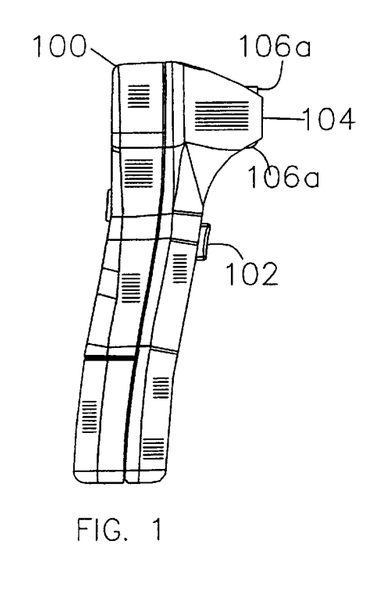
FIG. 1 is a side view of a measuring instrument that can be used with a device embodying the invention.

An example of such a medical instrument is shown in FIG. 1. The instrument 100 includes a trigger 102 for activating the device. When activated, the device emits light at one or more wavelengths from a nose portion 104. Light that is reflected or scattered from the patient is then collected by the nose portion 104 and analyzed to determine a condition of the patient.

Instruments like the one shown in FIG. 1 may require periodic calibration to maintain their accuracy. Over time, the amplitude and/or wavelength of light output by the light source within the instrument can vary due to environmental conditions, or simple aging of the light emitting elements. In addition, a detector of the instrument can have differing sensitivities depending upon environmental conditions or the age of the detector. For instance, a change in temperature of only a few degrees can significantly affect the sensitivity of a light detector.

For the above reasons, it is common to calibrate a medical instrument prior to taking a reading on a patient. Typically, the instrument is aimed at a calibration target having known optical properties. Light is then scattered or reflected by the calibration target and received back in the instrument. Because the calibration target has known optical properties, the instrument is able to perform a calibration operation to ensure that the instrument continues to deliver accurate results.

Also, some measuring instruments use a reference target as part of a measurement process. In such a device, the instrument is aimed at a reference target having known optical properties. Light from the instrument is scattered or reflected from the reference target, and a reading is taken. The results of the measurement operation conducted on the reference target can then be used as a standard or reference against which patient measurements are judged. For instance, the result of a patient reading could be derived by determining a difference or ratio between a patient reading and a reading of the reference target. Because the optical properties of the reference target are known, variations in light output or detector sensitivity can be accounted for by use of the reference target.

When such an instrument is used with human or animal patients, steps must be taken to ensure that use of the instrument does not contaminate or infect a patient. When the instrument is successively used to examine two different patients, steps must be taken to ensure that there is no cross contamination between the patients.

SUMMARY OF THE INVENTION

The invention is a device and method that can be used to calibrate or reference a measuring instrument for purposes of taking a measurement. When the instrument is for medical diagnostic purposes, the device may include a shield to prevent patient contamination or infection. In some embodiments, the device may comprise both an infection shield and a calibration or reference target with known optical properties integrated into a single unitary element.

A device embodying the invention is configured to be attached to the operative end of a measuring instrument. Once attached, the instrument may perform one or more measurement cycles using a calibration or reference target of the device having known optical properties. After a calibration/reference operation has been successfully performed, the target is removed while an infection shield of the device remains attached to the instrument to prevent contamination or infection. The device can then be used to carry out a measurement or examination of a patient or a material.

In a preferred embodiment, the device is configured such that removal of the target irrevocably destroys the portion of the target used to perform a calibration or reference operation. As explained more fully below, when such a device is used with a medical instrument which is configured to perform only a single patient reading after each calibration/reference operation, use of the device can help to ensure that patients are not contaminated or infected, and that no cross-contamination between patients is possible.

A method embodying the invention utilizes the calibration or reference target to calibrate a measuring instrument or to provide a reference reading prior to taking an actual measurement on a patient or an object. Then, a measurement is taken on a patient or object. The results of the calibration/reference measurement, and the results of the patient/object measurement are used together to calculate a result.

In one method embodying the invention, a reference target is first attached to an output end of a measuring instrument. A first measurement is then taken with a light source of the measurement instrument turned off. This is called a dark reference reading. Next, a measurement is taken on the reference target with the light source turned on. This is termed a reference reading. The reference target is then removed from the measurement instrument, and a first measurement is conducted on a patient or an object with the light source of the instrument turned off. This is termed a dark object reading. Next, a patient or object measurement is conducted with the light source turned on. This is termed an object reading. A ratio is then created with a difference between the object reading and the dark object reading in the numerator, and a difference between the reference reading and the dark reading being in the denominator. By creating a ratio of the differences, any variation in the light output of the measurement instrument or of the detector sensitivity cancels out to provide an accurate measurement result.

In addition, the reference reading, dark reference reading, skin reading and dark skin reading can all be corrected for "stray light." The correction for stray light also helps to ensure that the measurement reading is more accurate. A method and formula for calculating and correcting for stray light is provided in the detailed description below.

Additional advantages, objects, and features of the invention will be set forth in part in the description which follows, and in part will become apparent to those having ordinary skill in the art upon examination of the following, or may be learned from practice of the invention. The objects and advantages of the invention may be realized and attained as particularly pointed out in the appended claims.

BRIEF DESCRIPTION OF THE DRAWINGS

Preferred embodiments of the invention will be described in conjunction with the following drawing figures, wherein like reference numerals refer to like elements, and wherein.

DETAILED DESCRIPTION OF PREFERRED EMBODIMENTS

A device embodying the invention may be comprised of several parts. The first part is simply a device for anchoring an infection shield and a calibration or reference target to a measuring instrument. If the instrument is like the one shown in FIG. 1, a shield holder 110, as shown in FIG. 2, can be used to attach an infection shield and a calibration or reference target to the nose portion 104 of the instrument 100.

The terms "calibration target" and "reference target" are used interchangeably in the following text to refer to a target having known optical properties. The invention is applicable to both calibration targets and reference targets, and use of either term should not be construed as limiting.

Figure 2:
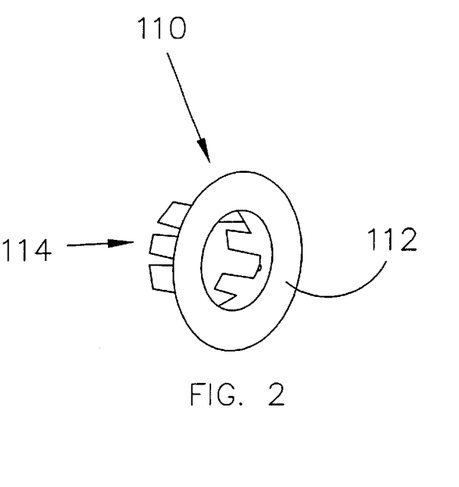
FIG. 2 is a perspective view of a portion of an embodiment of the invention.
Figure 3:
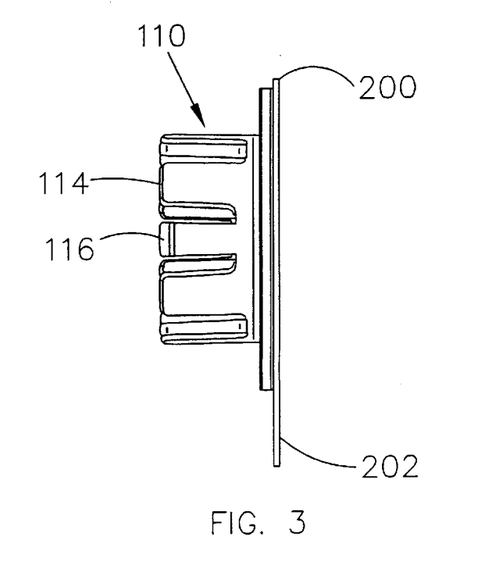
FIG. 3 is a side view of an embodiment of the invention.
Figure 4:
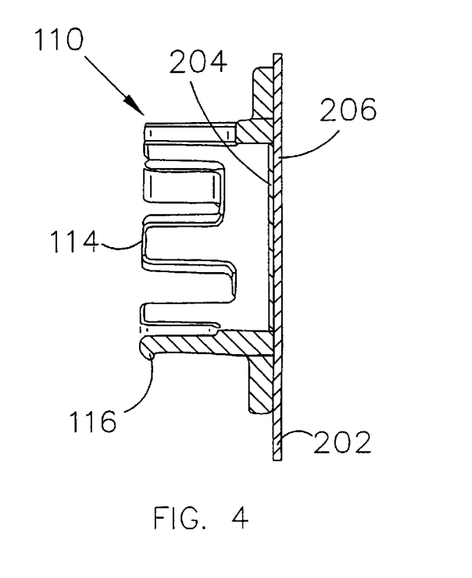
FIG. 4 is a sectional view of a second embodiment of the invention.

As seen in FIGS. 2–4, the shield holder 110 has a plurality of finger-like projections 114 arranged in a cylindrical shape. Some or all of the projections 114 may include a lip which is engageable with the nose portion 104 of the instrument 100 to attach the device to the instrument. If the shield holder 110 is made from a flexible material, such as a molded plastic, the shield holder 110 can be snapped onto the nose 104 of the instrument 100 so that the lips 116 engage the nose 104.

A multilayer combined infection shield and calibration target 200 can then be affixed to a front annular surface 112 of the shield holder 110. In a preferred embodiment of the invention, the combined infection shield and calibration target 200 is attached to the shield holder 110 with a layer of adhesive. The combined infection shield and calibration target 200 may include a user graspable tab 202 for removing the calibration target after a calibration or reference operation has been performed.

Figure 12:
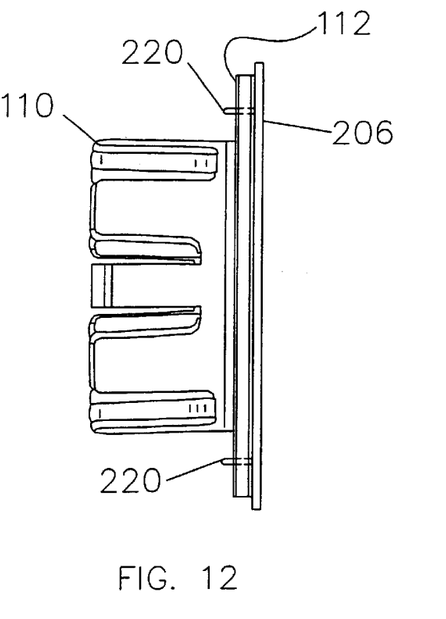
FIG. 12 is a side view of another embodiment of the invention.

Of course a calibration target 200 could also be mechanically attached to the shield holder 110 by any type of mechanical attachment mechanism such as staples, clips, pins, etc. FIG. 12 shows an embodiment where a calibration target 206 is attached to a shield holder 110 with a plurality of pins 220 arranged around the periphery of the shield holder 110.

In an alternate embodiment, as shown in FIG. 4, an infection shield 204 may be separately mounted to the shield holder 100. A calibration target 206 could then be attached to the front annular surface 112 of the shield holder 110 via an adhesive layer or some type of mechanical attachment device. The calibration target 206 would include a user graspable tab 202 for removing the calibration target after a calibration or reference operation has been performed.

Figure 5:
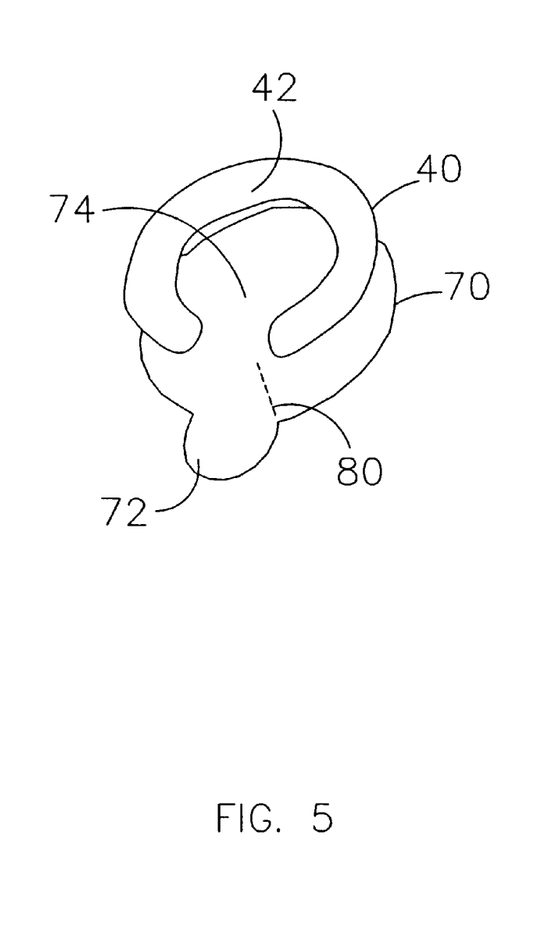
FIG. 5 is an exploded perspective view of a calibration target that can be used with an embodiment of the invention.

A calibration or reference target embodying the invention is shown in FIG. 5. The target includes a calibration layer 70 having a central portion 74 with known optical properties. A user graspable tab 72 is formed as a part of the calibration layer 70. Also, a double-sided adhesive layer 40 is used to attach the calibration layer 70 to a shield holder 110, as shown in FIG. 4. In alternate embodiments, the adhesive layer 40 can be used to attach the calibration layer 70 to a shield layer which is then attached to the shield holder 110, as shown in FIG. 3. In still other embodiments, the double-sided adhesive layer 40 could be replaced with an adhesive that is applied to the calibration layer 70 or a shield holder 110 in a liquid, gel or paste form.

The calibration layer 70 and the double-sided adhesive layer 40 are carefully constructed so that when the calibration target is removed from a shield holder, the target portion 74 in the center of the calibration layer 70 will tear in a predetermined manner. To that end, the calibration layer 70 may include a reduced strength portion 80, which could be a slit, a perforation or a crease. The reduced strength portion 80 in the embodiment shown in FIG. 5 is a perforation that extends from a peripheral edge of the calibration layer 70, towards the central area 74. When a user grasps the tab 72 and pulls on the tab to remove the calibration layer 70 from a shield holder, the calibration layer 70 will tend to tear along the reduced strength portion 80.

In the embodiment shown in FIG. 5, the adhesive layer 40 has a horseshoe shape such that a portion of the calibration layer 70 having the reduced strength portion 80 is aligned with the gap in the adhesive layer 40. Also, in a preferred embodiment, a first side 42 of the adhesive layer 40 will have a relatively low adhesive strength, and the opposite side of the adhesive layer 40 will have a greater adhesive strength. In this configuration, the lower adhesive strength side 42 of the adhesive layer 40 is used to attach the calibration layer 70 to a shield holder. When a user pulls on the tab 72 to remove the calibration layer 70, the lower adhesive strength side 42 will separate from the shield holder before the calibration layer 70 separates from the higher adhesive strength side of the adhesive layer 40. Also, because of the gap in the adhesive layer 40, the portion of the calibration layer immediately to the right of the reduced strength portion 80 will tend to remain attached to the shield holder while the portion of the calibration layer 70 adjacent the tab and located beneath the gap in the adhesive layer 40 will pull upward and away from the shield holder. This will cause the calibration layer 70 to begin to tear along the reduced strength portion 80. As the user continues to pull on the tab 72, the tearing of the calibration layer 70 will tend to continue across the center portion 74 having the optical properties used to perform a calibration operation.

If a liquid, gel or paste adhesive is used to attach the calibration layer 70 to a shield holder 110, there will be no need to have varying adhesive strengths. However, in such an embodiment it would be advantageous if the adhesive had a greater affinity for the calibration layer 70 than for the shield holder 110. In this case, most, if not all, of the adhesive would remain attached to the calibration layer 70 as it is removed from the shield holder 110. Thus, no adhesive remaining on the shield holder 110 would contact the skin of a patient or a surface to be measured when the instrument and attached shield holder 110 are used to take a measurement.

Similarly, if some type of mechanical attachment mechanism is used to attach the calibration layer 70 to a shield holder 110, it may be advantageous if the mechanical attachment mechanism is more firmly attached to the calibration layer 70 than to the shield holder 110. This would result in the attachment mechanism being removed from the shield holder along with the calibration layer, leaving the shield holder 110 free of any protrusions when used to take a measurement. For instance, in the embodiment shown in FIG. 12, the pins 220 attaching the calibration target 206 to the shield holder 110 could be firmly attached to the calibration target. The cylindrical shafts of the pins 220 would extend through the annular portion 112 of the shield holder 110. Ends of the pins 220 that protrude out the back side of the annular portion 112 could have a slightly enlarged diameter, thus holding the pins 220 and the attached calibration target 206 firmly to the shield holder 110. When the user pulls the calibration target 206 away from the shield holder 110, the pins 220 will pull out of the holes in the annular portion 112. By arranging the pins in a particular orientation with respect to the user graspable tab 202 of the calibration target 206, the calibration target can be caused to tear or separate in a predetermined manner.

Once a calibration layer 70 has been completely removed from a shield holder, the central portion 74 of the calibration layer 70 should be irrevocably damaged so that the calibration layer 70 cannot be re-used for a new calibration operation. In the embodiment as shown in FIG. 4, because the side of the adhesive layer 40 in contact with the calibration layer 70 has a greater adhesive strength than the side 42 which was attached to the shield holder, all of the adhesive layer should remain attached to the calibration target and be removed from the shield holder along with the calibration layer 70.

As mentioned above, the calibration target shown in FIG. 5 is intended to be used with a shield holder 110 as shown in FIG. 4. This type of shield holder 110 includes its own integral infection shield 204.

Figure 6:
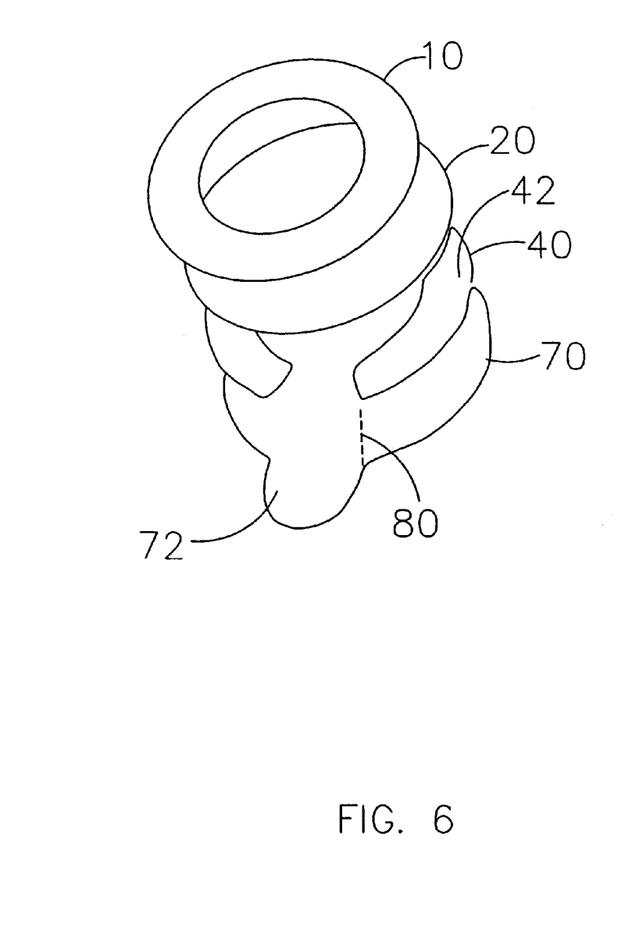
FIG. 6 is an exploded perspective view of a calibration target and an infection shield that can be used with an embodiment of the invention.

In an alternate embodiment, as shown in FIG. 6, both a calibration target and an infection shield are attached to the exterior of a shield holder. In this embodiment, a first double-sided adhesive layer 10 is attached to a front edge 112 of a shield holder 110, like the one shown in FIG. 3. The opposite side of the adhesive layer 10 is then attached to a transparent infection shield 20. An adhesive layer 40 and a calibration layer 70 are then attached to the infection shield 20. The adhesive layer 40 and the calibration layer 70 have generally the same properties as those described for the embodiment shown in FIG. 5. That is, a first side 42 of the adhesive layer 40 has a relatively low adhesive strength, and the opposite side of the adhesive layer, which is attached to the calibration layer 70, has a greater adhesive strength. Thus, when a user pulls the tab 72 of the calibration layer 70 and removes the calibration layer, both the calibration layer and the adhesive layer 40 are removed. This leaves just the infection shield 20 attached to the shield holder 110 and the instrument 100. Of course the double-sided adhesive layers 10 and 40 could also be replaced with a liquid, gel or paste adhesive, or with a mechanical attachment device, as described above.

The instrument can then be used to conduct a measurement on a patient with light generated by the instrument passing through the infection shield 20, striking the patient, and being reflected back through the infection shield 20 to the device. After a patient measurement has been completed, the shield holder 110 and the attached infection shield 20 are removed from the instrument 100 and disposed of.

The calibration layer 70 can have a reduced strength portion 80 configured in many different ways. In the embodiments shown in FIGS. 5 and 6, the reduced strength portions extend from a peripheral edge towards a center 74 of the calibration layer 70. This encourages the calibration layer to tear across the center 74 of the calibration layer 70, which is the portion having optical properties used to calibrate a measuring instrument. The reduced strength portion 80 does not extend beyond the annular radial width of the adhesive layer 80 so that light cannot penetrate through the calibration layer 70 and affect a calibration or reference operation.

Figure 7:
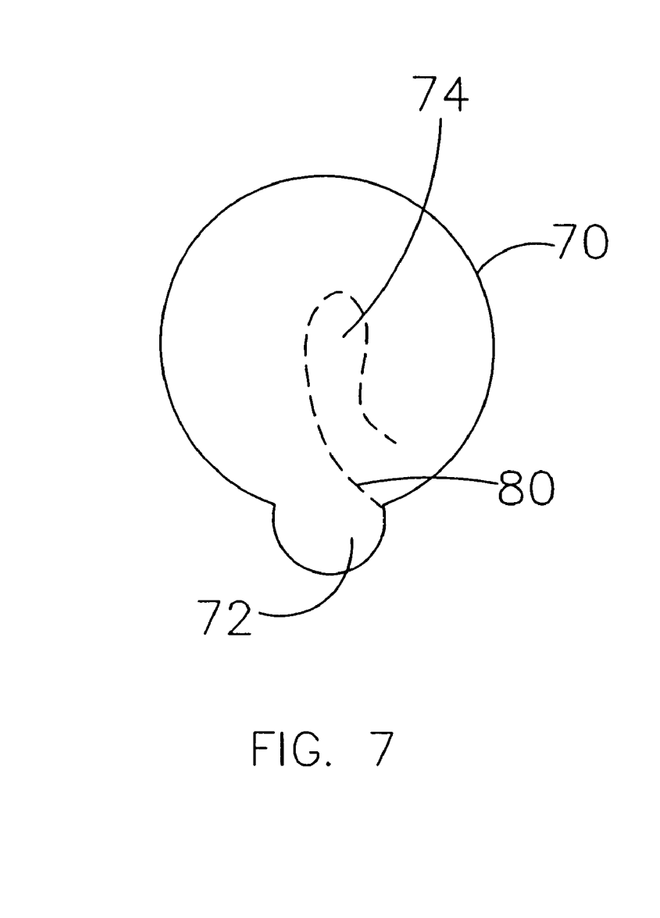
FIG. 7 is a plan view of a calibration target embodying the invention.
Figure 8:
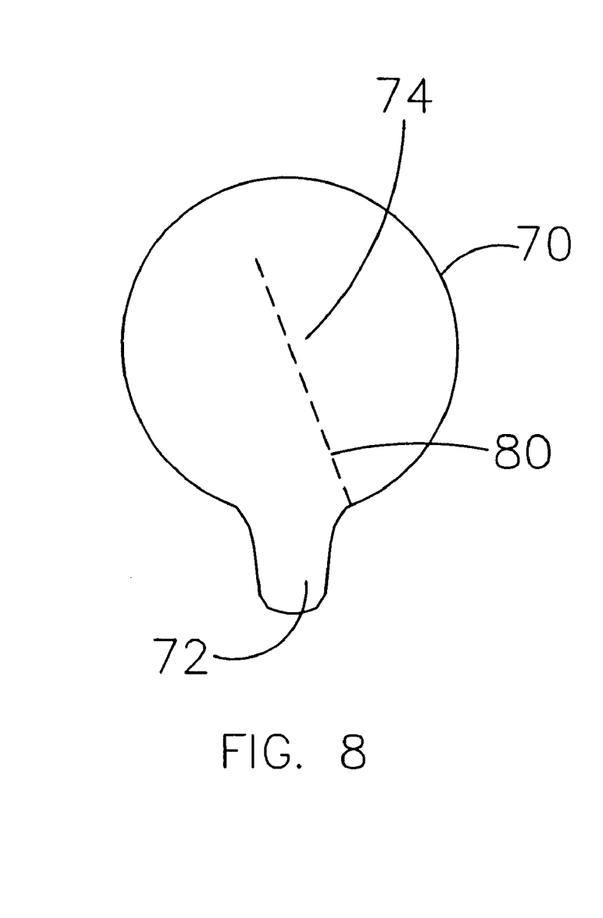
FIG. 8 is a plan view of another calibration target embodying the invention.

In alternate embodiments, as shown in FIGS. 7 and 8, the reduced strength portion can have different configurations. In the embodiment shown in FIG. 7, the reduced strength portion 80 traverses a path across the central region 74 of the calibration layer 70. In the embodiment shown in FIG. 8, the reduced strength portion 80 proceeds in a direct line across the center 74 of the calibration layer 70. Each of these embodiments is intended to ensure that as the calibration layer 70 is removed, the central portion 74 used to calibrate the instrument is altered in a destructive manner so that the calibration layer cannot be reused.

Figure 11:
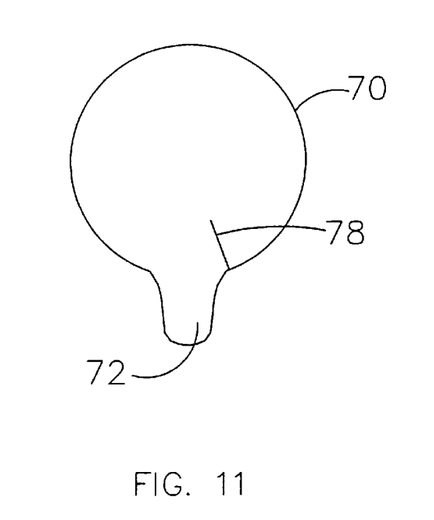
FIG. 11 is a plan view of another calibration target embodying the invention.

In still other embodiments, a cutting device could be incorporated into the calibration layer 70, or into the shield holder 110 or the instrument itself. One such embodiment is shown in FIG. 11, where a wire or monofilament 78 is attached to or embedded in the calibration layer 70. The wire or monofilament 78 will cause the calibration layer 70 to tear in a predetermined manner when a user pulls on the tab 72. Although FIG. 11 shows the wire or monofilament extending only partway across the calibration layer 70, the wire or monofilament could extend further or completely across the calibration target 70. The wire or monofilament could also be arranged in a pattern, like the reduced strength portion 74 shown in FIG. 7.

Figure 13:
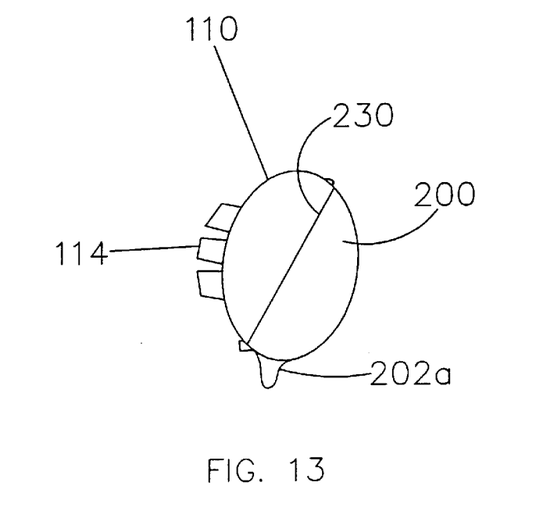
FIG. 13 is a perspective view of another embodiment of the invention.

In alternate embodiments a wire or monofilament could also be attached to the shield holder. In the embodiment shown in FIG. 13, a wire or monofilament 230 is stretched across the back of the calibration layer 200, with ends of the wire or monofilament being attached to the shield holder 110. Also, the wire or monofilament 230 could be replaced with any other type of cutting device that will cause the calibration layer 70 to tear or separate in a predetermined manner when being removed from a measuring instrument.

If the medical instrument 100 which is used in conjunction with a device embodying the invention is configured so that only a single patient measurement may be conducted after each calibration, a device embodying the invention can help to prevent patient infection or patient cross-contamination.

When a doctor or other medical personnel attempts to use the medical instrument, a shield holder with an infection shield and a calibration target will first be attached to the instrument 100. Next, a calibration operation will be performed. During the calibration operation, the instrument will emit light which is reflected from a central portion 74 of the calibration target. The reflected light is then received by the medical instrument and used to conduct a reference or calibration operation.

Once the calibration/reference operation is complete, the user will grasp a tab 72 on the calibration target and pull on the tab to remove the calibration target. This will cause the calibration target and any attached adhesive layer to be removed from the shield holder. The act of removing the calibration target will destroy at least the portion of the calibration target having the optical properties used to calibrate the instrument 100. Thus, it will be impossible to reuse the calibration target. The medical personnel would then proceed to conduct a patient measurement with the shield holder and an attached infection shield still attached to the instrument 100. The results of the measurement can then be noted or recorded.

Because the instrument will not perform a second patient measurement without first performing another calibration/reference operation, the medical personnel will be forced to remove both the shield holder and the infection shield and replace it with a new device that includes a new infection shield and a new calibration target. The medical personnel will be forced to perform another calibration operation before the device can be used to perform another patient measurement. For this reason, it should be impossible for the device to be used to take two measurements on two different patients using the same shield holder and infection shield. This prevents cross-contamination between different patients.

Also, an interlock mechanism in the nose of the measuring instrument may interact with a shield holder of a device embodying the invention to inform the instrument when the shield holder is removed. The instrument can then be configured so that no patient measurements can be performed once a shield holder has been removed from the instrument. This should discourage medical personnel from attempting to conduct a patient measurement without an infection shield in place, thereby reducing the opportunity for patient infection.

Figure 9:
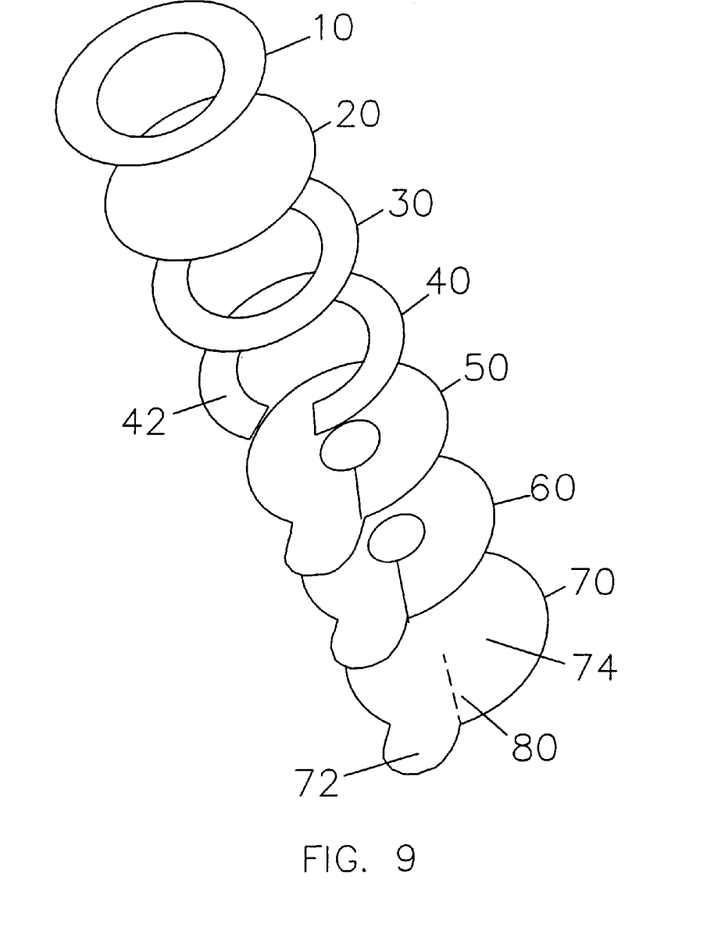
FIG. 9 is an exploded perspective view of a calibration target and infection shield that can be used with an embodiment of the invention.

In a preferred embodiment of the invention, the shield holder is configured as shown in FIG. 3, and a combined infection shield and calibration target 200 will be constructed as shown in FIG. 9. In this embodiment, a first double-sided adhesive layer 10 is used to attach the combined infection shield and calibration target to the shield holder 110. The opposite side of the double-sided adhesive layer 10 is adhered to a shield layer 20. Next, a clear release liner 30 is attached to the infection shield 20. The release liner 30 will remain permanently attached to the infection shield 20, but will provide a controlled release of the remaining portions of the combined infection shield and calibration target.

Next, a second double-sided adhesive layer 40 is attached to the release liner 30. As in the previous embodiments, a gap is formed in the adhesive layer 40. Next, a spacer layer 50 is attached to the opposite side of the second adhesive layer 40. The spacer layer 50 serves to space a calibration layer a precise distance from an emitting end of an instrument to which the device is attached. A third double-sided adhesive layer 60 then attaches a calibration layer 70 to the spacer layer 50.

The double sided adhesive layers 10, 40 and 60 could all be replaced with a liquid, gel or paste adhesive, or by a mechanical attachment device, as explained above.

The central portion 74 of the calibration layer 70 will be exposed to light emitted by an emission end of an instrument to which the device is attached. Also, reduced strength portions are formed in the spacer layer 50, the third double-sided adhesive layer 60 and the calibration layer 70. As explained above, the reduced strength portions cause the calibration layer 70 to tear in a predetermined manner when the calibration layer 70 is removed from the remaining portions of the device. Also, the reduced strength portions are oriented in a predetermined manner with respect to the gap in the second double-sided adhesive layer 40. Preferably, the reduced strength portions are positioned adjacent one side of the gap. When the device is oriented in this manner, pulling on the tab 72 of the calibration layer 70 causes the calibration layer to tear along the reduced strength portion 80 and to irrevocably damage the central portion 74 of the calibration layer 70.

Of course, the reduced strength portions could also be replaced by a cutting device, as explained above, to cause the calibration layer to tear or separate in a predetermined manner.

Figure 10:
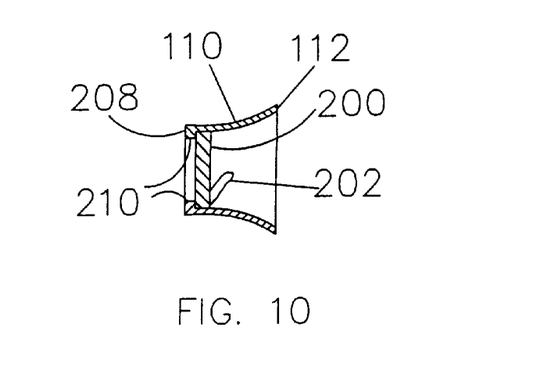
FIG. 10 is a sectional view of another embodiment of the invention.

Many variations of the above described embodiments are possible without departing from the spirit and scope of the invention. For instance, in the embodiment shown in FIG. 10, the narrower portion of the shield holder is to be attached to a measuring instrument, and the larger diameter flared portion 112 extends away from the device. A flexible annular ring of material 210 on the rear of the shield holder may engage projections 106a on the nose portion 104 of a measuring instrument 100, as shown in FIG. 1. In this embodiment, a combined infection shield and calibration target 200 is located adjacent the back side 208 of the shield holder 110, instead of being located on the front end 112. The combined infection shield and calibration target 200 still includes a user graspable tab 202 which can be pulled to remove the calibration target. This embodiment, like the embodiment shown in FIG. 4, could have an infection shield mounted on the shield holder and a separate target which is adhered to the shield holder or the infection shield.

In addition, although each of the embodiments shown in FIGS. 2–10 are generally circular or annular in shape, any other shape could be used without departing from the invention. For instance, the shield holder, infection shield and calibration target could be rectangular, square, or any other shape necessary to conform to the shape of the instrument to which the device is attached.

Also, the calibration layers 70 of the embodiments described above could have any type of optical properties used to conduct a calibration or reference operation. As mentioned above, use of the term "calibration target" in the specification and claims is intended to encompass both calibration targets and reference targets. Likewise, use of the term "calibration operation" is intended to encompass both calibration and reference operations.

In a preferred embodiment, the calibration layer would have a coating which has very specific reflectance properties. Furthermore, different devices embodying the invention might include different types of calibration layers having different reflectance properties. A calibration device embodying the invention could then be selected by a user based on a patient's skin tone or age, and the selected calibration target could be used to calibrate an instrument.

Also, although each of the embodiments described above have a user graspable tab attached to the calibration layer, other types of user graspable tab configurations are possible. For instance, instead of being a tab, a cord, a string or a ring of material could be attached to the calibration layer. For instance, in the embodiment shown in FIG. 13, the user graspable tab 202a is a loop of material whose ends are attached to the calibration layer 200. Each of these items is easy for the finger of a user to grasp and to pull. The invention is intended to include any type of user graspable tab, cord, string, ring, or other device that can be used to remove the calibration layer from the remaining portions of the device.

Furthermore, in the embodiments described above, an infection shield and a calibration target are attached to a shield holder, which in turn is attached to the instrument. Some embodiments of the device may not utilize a shield holder. In these embodiments, the infection shield and/or the calibration target may be directly attached to a measuring instrument. These embodiments may use an adhesive layer or a mechanical attachment device to attach the infection shield and the calibration target to the instrument.

Still further, if the instrument which the device is used with is not used for medical purposes, and infection or cross-contamination is not an issue, a device embodying the invention may simply comprise a calibration layer. The calibration target in FIG. 5 provides an example of such an embodiment.

A measurement instrument that could utilize a reference target as described above could be used to determine reflectance or scattering characteristics of a patient's skin. Such a device would typically incorporate a light source for illuminating a patient's skin, and some means for determining the intensity of reflected or scattered light at particular wavelengths. The device could be a detector coupled with an optical filter, or a spectrometer. The output of the detector or spectrometer would be a numerical count value representing the intensity of light at a particular wavelength.

In a method embodying the invention, the measuring instrument first takes readings against a reference target, then takes readings against the skin of a patient or the surface of an object. The patient or object readings are then compared with the reference target readings to provide a meaningful output value. This output value may be expressed as an optical density (OD). A formula for calculating an optical density in a method embodying the invention is shown below in Equation (1).

$$OD = -\text{Log}_{10} \frac{(Skin - SkinDark)_s}{(Ref - RefDark)_s} \quad (1)$$

In a method embodying the invention, the measuring instrument is used with the reference target to obtain two values. First, a reading is taken against the reference target with a light source of the instrument turned off. This is referred to as a dark reference reading, which is abbreviated as RefDark in Equation (1). Next, a reading is taken on the reference target with a light source of the measuring instrument turned on. This is referred to as a reference reading, which is abbreviated Ref in Equation (1). Both of these measurements would typically be conducted at a particular wavelength.

Next, two readings are taken on a patient's skin or on an object. The first reading is taken with the light source turned off to provide a dark skin reading. This is abbreviated SkinDark in Equation (1). Next, a reading is taken against the skin of the patient or on the object with the light source of the measuring instrument turned on to obtain a patient/object reading. This is abbreviated Skin in Equation (1). The dark skin reading is then subtracted from the skin reading to provide a corrected patient/object reading. The dark reference reading is also subtracted from the normal reference reading to provide a corrected reference reading. A negative logarithm is then taken of the ratio of the corrected patient reading to the corrected reference reading. This provides an optical density value which can be used to diagnose a condition of the patient.

In alternate methods embodying the invention, a plurality of dark skin readings and normal skin readings may be conducted at multiple different locations on a patient's skin. The difference between the normal skin reading and the dark skin reading at each of the different locations can then be averaged to provide the value for the numerator of Equation (1).

Furthermore, in alternative methods embodying the invention, two or more patient readings may be conducted at different wavelengths, and the results of each of the readings may provide a plurality of different optical density values that are then combined to determine a condition of the patient.

Still further, both the skin and reference readings described above may be corrected for "stray light." Theoretically, there is no light with a wavelength lower than 350 nm or with a wavelength higher than 850 nm. Signal levels detected at such wavelengths are considered "stray light." A method for correcting for stray light is described below with reference to Equation (2).

$$(I(\lambda))_s = \left( I(\lambda) - \left[ I(330) - \frac{I(330) - I(900)}{(900 - 300)} * (\lambda - 330) \right] \right) \quad (2)$$

If I(λ) represents a corrected skin reading or a corrected reference reading, as described above, these readings can be corrected for stray light using Equation (2) shown above. The correction for stray light requires that the intensity of light be measured at 330 nm to provide a value I(330), and that the intensity of light at 900 nm be measured to provide a value I(900). These values are then inserted in Equation (2), shown above, to provide a stray light corrected intensity value $(_s(\lambda))_s$. These stray light corrected intensity values for the corrected skin intensity and the corrected reference intensities are used in Equation (1) above to provide an optical density value which can be used to diagnose a condition of a patient.

Additional variations and alternative embodiments of the invention will become apparent to those skilled in the art upon reading the proceeding specification. These additional or alternative embodiments still fall within the scope of the invention as defined by the following claims.

What is claimed is:

1. A disposable calibration device, comprising:

a calibration layer; and an attachment device configured to attach the calibration layer to a measuring instrument such that the calibration layer will tear or separate in a predetermined manner when the calibration layer is removed from the attachment device.

2. The device of claim 1, wherein the calibration layer includes a reduced strength portion that helps to cause the calibration layer to tear or separate in a predetermined manner when the calibration layer is removed from the attachment device.

3. The device of claim 1, wherein the attachment device comprises an adhesive layer.

4. The device of claim 3, wherein the adhesive layer includes a peripheral section without adhesive, such that the adhesive of the adhesive layer extends around all but a portion of a periphery of the calibration layer.

5. The device of claim 4, wherein the calibration layer comprises a reduced strength portion that helps the calibration layer to tear or separate in a predetermined manner when the calibration layer is removed from the attachment device.

6. The device of claim 5, wherein the peripheral section of the adhesive layer without adhesive is aligned with the reduced strength portion of the calibration layer.

7. The device of claim 5, wherein the reduced strength portion extends from a position adjacent a peripheral edge of the calibration layer towards an inner portion of the calibration layer.

8. The device of claim 1, wherein the attachment device comprises at least one mechanical attachment device.

9. The device of claim 8, wherein the at least one mechanical attachment device is one of a staple, a pin, a clip, a screw and a clamp.

10. The device of claim 1, further comprising a cutter that causes the calibration layer to tear or separate in a predetermined manner when the calibration layer is removed from the attachment device.

11. The device of claim 10, wherein the cutter is one of a wire and a monofilament.

12. A disposable calibration device, comprising:

a release layer, a double-sided adhesive layer, wherein a first side of the adhesive layer is attached to a first side of the release layer; and a calibration target arranged on a second side of the adhesive layer.

13. The device of claim 12, wherein the adhesive layer has a greater affinity for the calibration target than for the release layer, such that when the calibration target is removed from the calibration device, substantially all of the adhesive layer will remain attached to the calibration layer and be removed from the release layer.

14. The device of claim 12, wherein the calibration target is configured such that the calibration target will tear or separate in a predetermined manner when the calibration target is separated from other portions of the calibration device.

15. The device of claim 12, wherein the calibration target includes a reduced strength portion configured such that the calibration target will tear or separate in a predetermined manner when the calibration target is removed from other portions of the calibration device.

16. The device of claim 15, wherein the reduced strength portion comprises one of a slit, a perforation, and a crease.

17. The device of claim 12, further comprising a cutter for causing the calibration target to tear or separate in a predetermined manner when the calibration target is removed from other portions of the calibration device.

18. The device of claim 17, wherein the cutter comprises one of a wire or a monofilament.

19. The device of claim 12, further comprising a shield layer that is arranged on a second side of the release layer.

20. The device of claim 12, wherein the release layer comprises a shield layer.

21. The device of claim 12, further comprising an attachment device arranged on a second side of the release layer, wherein the attachment device is configured to attach the calibration device to a measurement instrument.

22. The device of claim 12, wherein the adhesive layer extends around all but a portion of a periphery of the calibration target, and wherein the calibration target and the adhesive layer are oriented with respect to one another so that the adhesive layer aids tearing or separation of the calibration target in the predetermined manner.

* * * * *